United States Patent [19]

McCarthy et al.

[11] 4,108,853

[45] Aug. 22, 1978

[54] N,15-DIDEHYDRO-15-DEOXO-PYRIMIDINO-(4,5-b)RIFAMYCIN S

[75] Inventors: James R. McCarthy; Jimmie L. Moore, both of Midland, Mich.

[73] Assignee: The Dow Chemical Company, Midland, Mich.

[21] Appl. No.: 802,214

[22] Filed: May 31, 1977

[51] Int. Cl.$^2$ .................. C07D 241/36; A61K 31/505
[52] U.S. Cl. ..................................... 544/245; 424/251
[58] Field of Search .................... 424/251; 260/251 Q, 260/251 QA

[56] References Cited

PUBLICATIONS

Moore et al., Tetrahedron Letters, No. 50, pp. 4541–4544 (1976).

*Primary Examiner*—Jerome D. Goldberg
*Attorney, Agent, or Firm*—James W. Ambrosius

[57] ABSTRACT

The subject compound is prepared by an activated manganese dioxide oxidation of N,15-didehydro-15-deoxo-3,15-epi(methano(imino)rifamycin SV. The new compound has antimicrobial utility.

1 Claim, No Drawings

N,15-DIDEHYDRO-15-DEOXO-PYRIMIDINO-(4,5-b)RIFAMYCIN S

SUMMARY OF THE INVENTION

The subject compound, 1 below, is prepared by an activated manganese dioxide oxidation of the dihydropyrimidine (2 below), preparation described in *Tetrahedron Letters* 50, 4541 (1976), pursuant to the following equation:

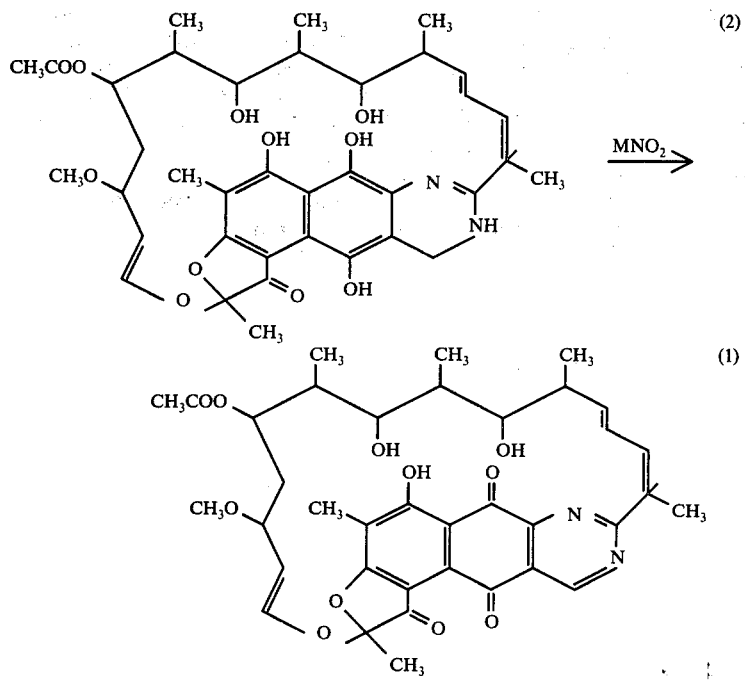

In practice, the dihydropyrimidine compound, 2, is dissolved in reagent methanol. To the resulting solution is added activated manganese dioxide in amount sufficient to oxidize the compound to the title compound, and the resulting suspension is refluxed. The progress of the reaction is followed by taking periodic aliquots of the reaction mixture, adding them to aqueous ascorbic acid, extracting with ethyl acetate and examining with tlc (chloroform:methanol (9:1)). The reaction requires about 3 hours for completion. The reaction mixture is then cooled, vacuum filtered, and the residue washed thoroughly with methanol. The filtrate is added to aqueous 5% ascorbic acid, diluted with sodium chloride brine and extracted with chloroform three times. The extracts are dried over sodium sulfate, filtered and concentrated to give a dark residue. The latter is dissolved in chloroform:methanol (90:10) and filtered through silica gel using the same solvent pair. The filtrate is treated briefly with crystalline citric acid monohydrate, washed with sodium chloride brine, dried over sodium sulfate, filtered and concentrated to give a dark residue. The latter is crystallized from ether to give dark crystals. A portion thereof is dissolved in reagent chloroform and oxidized by thoroughly washing with aqueous $K_3Fe(CN)_6$ solution. The chloroform layer is dried over sodium sulfate, filtered and concentrated to dryness. A concentrate of the residue is applied to a column of silica gel (Woelm, 70–230 mesh) packed and eluted with chloroform:methanol (98:2). The eluant is collected in small fractions and examined by tlc. The earlier fractions are combined and concentrated to give a residue which is crystallized from ether to give the pyrimidino compound, 1.

The present invention is also directed to a method for killing or controlling a microorganism inhibited by the subject compound 1 by applying an antimicrobially-effective amount of the compound to the microorganism or to the habitat inhabited by the microorganism. As used herein, the term "an antimicrobially-effective amount of the subject compound" refers to that amount which will effectively inhibit a microorganism inhibited by the subject compound. The compound described herein may also be used in an antimicrobial composition in combination with a pharmaceutical carrier well known to those skilled in the art.

DESCRIPTION OF SOME PREFERRED EMBODIMENTS

Example 1 —
N,15-Didehydro-15-deoxo-pyrimidino(4,5-b)-rifamycin S

A 2.5 g (3.5 mmol) quantity of the dihydropyrimidine, 2, was dissolved in 50 ml of reagent methanol. To this solution was added 5 g of activated manganese dioxide and the resulting suspension was refluxed. At 1 hour intervals, aliquots of the reaction mixture were added to aqueous ascorbic acid, extracted with ethyl acetate, and examined by tlc (chloroform:methanol (9:1)). After 3 hours, the reaction was complete. The reaction mixture was allowed to cool, was vacuum filtered, and the residue was washed thoroughly with methanol. The filtrate was added to 100 ml of aqueous 5% ascorbic acid, diluted with 40 ml of sodium chloride brine, and extracted with chloroform (3×60 ml). The extracts were dried ($Na_2SO_4$), filtered, and concentrated to give 2.3 g of dark residue. The residue was dissolved in chloroform:methanol (90:10) and filtered through 40 g of silica gel (Merck 60, 2.5 × 18 cm) using the same solvent pair. The filtrate was treated briefly with crystalline citric acid monohydrate, washed with sodium chloride brine, dried ($Na_2SO_4$), filtered and concentrated to give 2.3 g of dark residue. The residue was crystallized from ether to give 1.555 g of dark crystals having no mp. A 0.7 g portion of this material was dissolved in 50 ml of reagent chloroform and was oxidized by thorough washing with aqueous $K_3Fe(CN)_6$ solution (0.5 g in 50 ml). The chloroform layer was dried ($Na_2SO_4$), filtered, and concentrated to dryness. A concentrate of the residue was applied to an 80 g column of silica gel (Woelm, 70–230 mesh, 35 × 2.4 cm) packed and eluted with chloroform:methanol (98:2). The eluant was collected in 50 ml fractions and examined by tlc. The first four fractions were combined and concentrated to give 0.5 g of residue which was crystallized from ether to give 133 mg of the titular pyrimidino compound, homogenous by tlc: $R_f$ 0.57 [chloroform:methanol (98:2)]; ir (nujol): 3475, 1735, 1710, 1675, 1645, 1600, 1565, 1540 cm$^{-1}$; UV-VIS ($CH_3OH$): $\lambda_{max}$ 265 nm ($\epsilon$ 20,600), 280 nm ($\epsilon$ 20,700), 410 nm ($\epsilon$ 7,400), pmr ($CDCl_3$): $\delta$ 12.95 (S, 1H, exch. with $D_2O$, phenolic OH), $\delta$ 9.50 (S, 1H, Ar—H), $\delta$ 5.9–6.7 (M, 4H), $\delta$ 5.15 (dd, $J_{27,28}$ = 12.5, 1H, 28-H), $\delta$ 5.00 (d, J = 10, 1H, 25-H), $\delta$ 3.07 (S, 3H, $OCH_3$), $\delta$ 2.37 (S, 6H, 14-$CH_3$ and 30-$CH_3$), $\delta$ 2.04 (S, 3H, 36-$CH_3$), $\delta$ 1.78 (S, 3H, 13-$CH_3$), $\delta$ 0.5–1.1 (3d, J = 7, each 3H, methyl groups). Calc'd for $C_{36}H_{44}N_2O_{11}$: C, 64.76; H, 6.29; N, 3.98. Found: C, 64.59; H, 6.11; N, 3.79.

EXAMPLE 2

The titular compound has antimicrobial utility, and, in practice, is useful in combination with conventional pharmaceutical carriers. Thereby, the active compound may be applied directly or indirectly to the microorganisms which it is desired to control. In a conventional in vitro agar Petri dish dilution test for determining antimicrobial activity, the compound of this invention had a minimum inhibitory concentration (MIC) in parts per million (ppm) of 1 against *S. aureus* 6533 and 100 against *S. marscesens*.

What is claimed is:
1. The compound N,15-didehydro-15-deoxo-pyrimidino(4,5-*b*)rifamycin S.

* * * * *

UNITED STATES PATENT AND TRADEMARK OFFICE
CERTIFICATE OF CORRECTION

PATENT NO. : 4,108,853
DATED : August 22, 1978
INVENTOR(S) : James R. McCarthy, et al.

It is certified that error appears in the above-identified patent and that said Letters Patent are hereby corrected as shown below:

Column 1, line 10, Formula should read as follows:

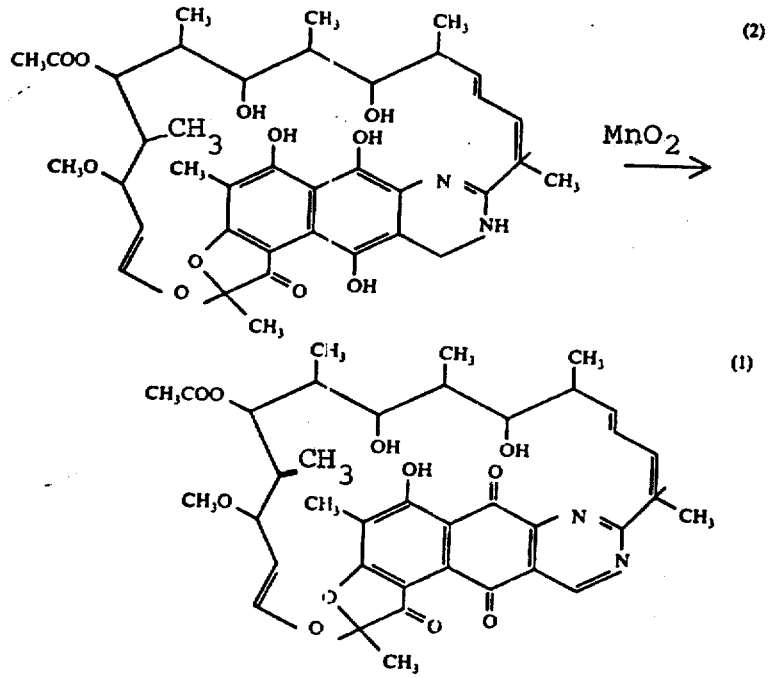

Signed and Sealed this

Third Day of April 1979

[SEAL]

Attest:

RUTH C. MASON
Attesting Officer

DONALD W. BANNER
Commissioner of Patents and Trademarks